(12) United States Patent
Piette et al.

(10) Patent No.: US 8,394,074 B2
(45) Date of Patent: Mar. 12, 2013

(54) UNDERGARMENT FOR INCONTINENT PERSON AND TREATMENT DEVICE CONNECTED TO AN UNDERGARMENT

(75) Inventors: François Piette, Colombes (FR); Roger Tambrun, La Celle Saint Cloud (FR)

(73) Assignee: Universite Pierre et Marie Curie (Paris 6), Paris (FR)

( * ) Notice: Subject to any disclaimer, the term of this patent is extended or adjusted under 35 U.S.C. 154(b) by 672 days.

(21) Appl. No.: 12/441,026

(22) PCT Filed: Sep. 12, 2007

(86) PCT No.: PCT/FR2007/051926
§ 371 (c)(1),
(2), (4) Date: Sep. 10, 2009

(87) PCT Pub. No.: WO2008/031994
PCT Pub. Date: Mar. 20, 2008

(65) Prior Publication Data
US 2010/0010459 A1    Jan. 14, 2010

(30) Foreign Application Priority Data
Sep. 13, 2006 (FR) .................................... 06 53719

(51) Int. Cl.
*A61F 5/458* (2006.01)
(52) U.S. Cl. .................. 604/353; 604/322; 604/352
(58) Field of Classification Search .......... 604/347–353, 604/322, 318
See application file for complete search history.

(56) References Cited

U.S. PATENT DOCUMENTS

| | | | | | |
|---|---|---|---|---|---|
| 1,761,609 | A | * | 6/1930 | Becker | 604/347 |
| 2,074,119 | A | * | 3/1937 | Boysen et al. | 66/175 |
| 2,277,043 | A | * | 3/1942 | Cohn | 604/348 |
| 2,337,648 | A | * | 12/1943 | Clarke | 4/451 |
| 2,749,558 | A | * | 6/1956 | Lent et al. | 4/454 |
| 2,944,551 | A | * | 7/1960 | Breer | 604/73 |
| 3,043,307 | A | * | 7/1962 | Weston | 604/349 |
| 3,161,198 | A | * | 12/1964 | Moxley | 604/353 |
| 3,290,752 | A | * | 12/1966 | Ormand | 28/156 |
| 3,508,234 | A | * | 4/1970 | Snyder | 340/573.5 |
| 3,522,808 | A | * | 8/1970 | Worcester | 604/347 |
| 3,577,989 | A | * | 5/1971 | Anderson | 604/348 |
| 3,626,941 | A | * | 12/1971 | Webb | 604/291 |
| 4,210,528 | A | * | 7/1980 | Coviello et al. | 210/605 |
| 4,224,610 | A | * | 9/1980 | Quinby | 340/614 |
| 4,791,686 | A | * | 12/1988 | Taniguchi et al. | 4/448 |

(Continued)

FOREIGN PATENT DOCUMENTS

| | | |
|---|---|---|
| DE | 42 12 639 A1 | 8/1992 |
| EP | 0 002 115 | 5/1979 |

(Continued)

OTHER PUBLICATIONS

DE 4212639, Ernst Paduch, Aug. 20, 1992, Machine Translation.*

(Continued)

*Primary Examiner* — Melanie Hand
*Assistant Examiner* — Paula Craig
(74) *Attorney, Agent, or Firm* — O'Brien Jones, PLLC

(57) ABSTRACT

The present invention relates to an undergarment (1) comprising: a supporting part (2) which surrounds at least the hips and the top of each thigh; and a flexible collecting bag (10) positioned in the crotch.

29 Claims, 4 Drawing Sheets

U.S. PATENT DOCUMENTS

Figure 1:
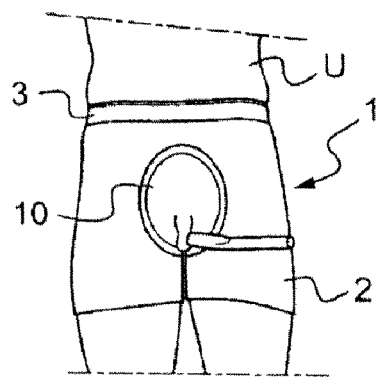

| | | | | |
|---|---|---|---|---|
| 4,886,508 | A | * | 12/1989 | Washington ................ 604/327 |
| 4,904,387 | A | * | 2/1990 | Jordan ........................ 210/605 |
| 4,982,462 | A | * | 1/1991 | Wada ............................... 4/546 |
| 5,002,541 | A | * | 3/1991 | Conkling et al. ............. 604/319 |
| 5,342,583 | A | | 8/1994 | Son |
| 5,558,654 | A | * | 9/1996 | Hardy .......................... 604/322 |
| 5,681,297 | A | | 10/1997 | Hashimoto et al. |
| 5,792,132 | A | * | 8/1998 | Garcia .................... 604/385.01 |
| 5,809,586 | A | * | 9/1998 | Kitamura ......................... 4/443 |
| 6,110,159 | A | * | 8/2000 | Tsujita et al. ................. 604/387 |
| 6,236,951 | B1 | * | 5/2001 | Payne et al. ................... 702/116 |
| 6,238,378 | B1 | * | 5/2001 | Perez ............................ 604/317 |
| 6,293,937 | B2 | * | 9/2001 | Matsushita et al. ........... 604/396 |
| 6,394,988 | B1 | * | 5/2002 | Hashimoto .................. 604/355 |
| 6,641,567 | B1 | * | 11/2003 | Williams ...................... 604/327 |
| 6,991,669 | B1 | * | 1/2006 | Partridge et al. ................ 75/313 |
| 7,131,964 | B2 | * | 11/2006 | Harvie .......................... 604/347 |
| 7,498,478 | B2 | * | 3/2009 | Long et al. ................... 604/361 |
| 2002/0010446 | A1 | | 1/2002 | Maimets |
| 2004/0078219 | A1 | * | 4/2004 | Kaylor et al. ..................... 705/2 |
| 2004/0143229 | A1 | * | 7/2004 | Easter .......................... 604/322 |
| 2007/0038194 | A1 | * | 2/2007 | Wada et al. ................... 604/353 |

FOREIGN PATENT DOCUMENTS

| | | |
|---|---|---|
| JP | 54-077457 A | 6/1979 |
| JP | 54-074313 | 12/1980 |
| JP | 05-005127 | 1/1993 |
| JP | 06-054874 A | 3/1994 |
| JP | 07-124189 A | 5/1995 |
| JP | 09-173392 A | 7/1997 |
| JP | 2003-111788 A | 4/2003 |
| JP | 2003-210508 A | 7/2003 |
| JP | 2004-135962 A | 5/2004 |
| JP | 2005-160834 A | 6/2005 |
| JP | 2005-538803 A | 12/2005 |
| WO | WO 91/04714 | 4/1991 |
| WO | 2004/026194 A1 | 4/2004 |

OTHER PUBLICATIONS

Written Opinion of the international Searching Authority issued Mar. 13, 2009, in PCT/FR2007/051926, with English translation of Written Opinion obtained from WIPO Patentscope® website .

International Search Report in PCT/FR2007/051926 having a mailing date of Feb. 15, 2008.

Office Action mailed on Apr. 10, 2012 by the Japanese Patent Office, for co-pending JP Application No. 2009-527870, filed Apr. 2, 2012, with English Translation.

English language abstract for JP-2003-111788-A.

English language abstract for JP-2005-160834-A.

Office Action issued in Japanese Application No. 2009-527870, Mailing No. 532538, Mailing Date: Aug. 7, 2012.

* cited by examiner

UNDERGARMENT FOR INCONTINENT PERSON AND TREATMENT DEVICE CONNECTED TO AN UNDERGARMENT

This is a national stage application of PCT/FR2007/051926, filed internationally on Sep. 12, 2007, which claims priority to French Application No. FR 06 53719, filed in France on Sep. 13, 2006.

The present invention relates to aids for people with incontinence.

Total incontinence, urinary incontinence only, or urinary and fecal incontinence, affects many people in France and worldwide, among whom are a particularly high number of elderly patients receiving long-term care in hospital or in retirement homes.

This deficiency often comes with a major loss of independence for patients who are confined to bed at night and seated in an armchair throughout the day. Some of these patients may also suffer from Alzheimer's disease.

For affected patients, such a situation is a source of discomfort and irritation and aggravation of skin lesions.

Staff often arrive too late, given the very short amount of time available to those afflicted by instability of the bladder, which can be less than a minute, and the numerical shortage of staff members frequently makes it impossible to answer the calls of all patients.

It is also difficult to delay the bladder action by medical treatment designed to inhibit contractions of the bladder because treatment can be poorly received in those with Alzheimer's disease, or by perineal re-education, which would require the cooperation and learning of the patient, which are again difficult in the case of Alzheimer's disease or other similar diseases.

To solve these problems it is common practice to give the patient a disposable diaper. For a minimum level of comfort, the patient must have at least four disposable diapers each day, to which extra diapers may be added ad-hoc if necessary.

It is difficult to further reduce the number of daily diapers because of the fact that the contact of the skin of the perineum with urine and fecal matter is both uncomfortable and brings with it a risk of skin irritation which can lead to cutaneous or dermal abrasion.

Fitting such diapers has a considerable cost both in terms of material and personnel. Moreover, frequent changes of diapers tend to be disliked by patients because of the loss of dignity this entails.

Furthermore, fitting diapers every day can make the staff members in charge of this work feel undervalued. This can lead to difficulties in recruitment and make it impossible to increase the number of beds to meet the demands of the population.

American patent application US 2002/0010446 discloses a system for washing a person confined to bed, using special bedding. The person wears a garment which covers an undergarment comprising a hole in the perineal region, to which a collecting bag is attached. The excreta evacuation system disclosed is very expensive, requiring highly specialized bedding. Furthermore, the numerous points of injection of washing water supported by the garment mean that the system greatly restricts the patient's freedom. The seal around the thighs and waist can also result in heavy contamination of the body between the seals, which requires energetic washing of the region between the seals. US 2002/0010446 is therefore unsuitable for the elderly.

International application WO 91/04714 discloses a catheter for a man or woman, which catheter is capable of collecting and absorbing a liquid by means of a device placed in the underpants or outside of the underpants. The system disclosed is active and is similar to a traditional absorbent diaper capable of absorbing several urinary evacuations. Its cost of use is relatively high.

German patent application DE 4 212 639 discloses a woman's undergarment comprising a hole situated in the perineal region of the user. Evacuation is via a cap. DE 4 212 639 does not teach washing or detection and does not describe any maintenance of the bag, which can make the use of the device uncomfortable for the user.

American patent U.S. Pat. No. 5,342,583 discloses an apparatus for collecting a patient's urine. It consists of a garment comprising a hole for accommodating a device fitted with a urine evacuation means. The disclosed system is operated by an automatic nonprogrammable system with no monitoring of the patient and no possibility of varying the washing cycles. Furthermore, the configuration of the device does not offer comfortable, completely safe use for the patient. The nature of the washing action performed with this device makes it an unsuitable apparatus for elderly people.

There is therefore a need to make it easier to care for patients suffering from incontinence and to improve their comfort and cleanliness.

The present invention seeks to meet this need and proposes, in one of its aspects, an undergarment, comprising:
 a supporting part surrounding at least the hips and the top of each thigh, and
 a flexible collecting bag positioned in the crotch.

The supporting part may advantageously comprise an opening in the crotch and the collecting bag can be positioned at least partly in this opening.

The undergarment according to the invention reduces or avoids the use of conventional disposable diapers and therefore considerably diminishes incontinence care costs both in terms of materials and staff.

The undergarment of the invention can be very light, being very easy for the user to wear and causing very little discomfort.

The undergarment is advantageously worn directly on the patient's body, in contact with the skin. The undergarment may in particular not cover any other garment, either partly or totally.

At the same time, the invention significantly reduces, potentially to zero, the time lag between micturition or defecation and the processing of the corresponding excreta. The term "excreta" covers both urine and fecal matter.

The invention can allow the patient to rest on conventional bedding.

Lastly, the undergarment of the invention offers increased comfort and makes procedures that can undermine the dignity of the patient less frequent.

The undergarment of the invention can be for female, male or mixed use.

The undergarment of the invention can allow the user to move about in a lying position, or when sitting in an armchair, or when standing, and to change position comfortably and easily.

The collecting bag may or may not be in contact with the skin around the opening. Contact with the skin can be used to make a seal if necessary.

The collecting bag can cover the perineal region, and in particular both the pubic and anal regions of the user, in such a way as to collect both urine and fecal matter.

The collecting bag can define an internal volume of for example between 500 and 2000 $cm^3$ maximum, in the full condition.

The undergarment may have an evacuation tube connected through an evacuation orifice to the collecting bag. The evacuation tube can be placed in a channel within the undergarment. The collecting bag can be made in one piece integral with the evacuation tube. As a variant, the tube may be a separate component which is fitted onto the collecting bag by adhesive bonding or welding, for example. The evacuation tube may comprise a funnel-shaped connecting portion connecting it to the collecting bag so as to facilitate the evacuation of the matter.

The evacuation tube may comprise an end, remote from the collecting bag, that is configured to be connected to an excreta processing device. This end may for example comprise a threaded end or a quick release coupling.

The evacuation tube may advantageously be flexible.

Means of attachment may be provided to allow the evacuation tube to be attached to the supporting part, e.g. toward the waist.

The undergarment may comprise a cap for closing the evacuation tube when the latter is not connected to a processing device. The closure cap may be attached to the undergarment.

The closure cap may comprise a moisture detector, the latter comprising for example a visual and/or audible alarm configured to be triggered when a moisture threshold is exceeded. This alarm may comprise an autonomous battery supply which may be built into the cap if required.

The undergarment may also comprise an injection tube that connects through an injection orifice into the collecting bag, in order to be used for example when injecting a washing liquid and/or a lubricant and/or to allow air to be blown through the bag.

The evacuation and injection tubes may be joined together, particularly for part of their width. These tubes may be made for example by coextrusion or engaged in a common sheath.

The collecting bag may be made by injection molding of plastic material, particularly a flexible thermoplastic such as a polyolefin such as low-density polyethylene. The material used may be compatible with prolonged contact with the skin, and may especially be non-allergenic.

The undergarment may comprise a seal inserted between the collecting bag and the supporting part, such as a silicone seal. The use of this seal can improve the attachment of the bag to the supporting part and/or improve the adhesion of its periphery to the skin.

The collecting bag may be made in such a way that it can be separated from the supporting part.

If required, the collecting bag need not be fixed to the supporting part, but rather be held to the latter simply by the tightness with which the supporting part is held against the skin.

In a variant, the undergarment may comprise means for the removable connection of the collecting bag to the supporting part, such as at least one hook-and-loop tape, a zipper, press studs, one or more straps, or hooks. The connection means may advantageously be located on a face of the bag turned away from the skin in order not to be uncomfortable for the patient.

The collecting bag does not have to be made of the same material as the supporting part.

The supporting part may be made of a stretch material, which can increase the comfort and, where necessary, keep the collecting bag more securely against the skin around the opening.

The supporting part may be at least partly made of a textile material or made of a nonwoven, preferably a material that is neither airtight nor vapor-tight, so as to allow the skin to breathe.

The supporting part may be made of a washable material if required.

The supporting part may be made with a variety of structures and may comprise two or more superposed layers, which may make it possible to integrate between these layers elements to improve the comfort of the undergarment and/or elements useful for cleaning it.

The undergarment may thus comprise, in an illustrative embodiment of the invention, a plurality of inflatable cells positioned between the two superposed layers that can be connected to each other in order to be inflated by a single inflation means. Inflating the cells can facilitate evacuation, washing and drying.

The inner layer of the supporting part may be elastic, with gentle support, being comfortable, and the outer layer may be elastic with firmer support.

The undergarment may also be configured to permit some ventilation between the two superposed layers.

The undergarment need contain no absorbent material.

The undergarment may comprise tubes connected to the collecting bag. These tubes may lead to a system of connection to a processing device. This connection system may comprise magnetic engagement.

Evacuation of the urine and fecal matter may be through the same orifice of the collecting bag.

The connection system may comprise an electrical contact for informing the processing device about the status of the connection.

The connection system may comprise a plug guide.

The invention further relates, in another of its aspects, to a device for processing the excreta of at least one patient, comprising at least one excreta presence sensor and at least one system for connection to an undergarment as defined above, which processing device evacuates the excreta from the collecting bag on the basis of the information supplied by the sensor.

The processing device may in particular comprise at least one odor sensor.

The processing device may comprise a microprocessor or microcontroller configured to analyze the information supplied by the sensor and run a processing cycle on the basis of this information.

The interface between carers and the processing device may comprise manual-type actuators, dynamic data and monitoring screens, and safety alarms.

The processing cycle may comprise the evacuation of the excreta, washing and optionally drying and/or the injection of a lubricant or other compounds to improve comfort, for example.

The processing device may comprise an air processing unit configured to blow air through the collecting bag, especially with a variable flow rate, especially permanently or essentially permanently. That the air is blown "permanently or essentially permanently" should be understood as meaning that there may be interruptions to the air flow, but that these will preferably not be longer than around 2 hours.

The air flow may thus preferably be effective and continuous or at least half or even three quarters of the period of use of the processing device and of the associated undergarment, particularly when the patient is lying down or sitting.

The processing device may be configured in such a way that, if an odor that may be linked to defecation is, detected, a greater amount of air is blown for a predefined period, for example between 15 seconds and 2 minutes. If the odor persists, optionally after blowing a further, increased amount of air, a processing cycle may be commenced.

The processing device may be configured to inflate all or some of the abovementioned inflatable cells before the excreta is evacuated, e.g. as soon as odors are detected.

The processing device may comprise a container for receiving the evacuated excreta and/or at least one grinding pump. The grinding pump or pumps may be built into the device and/or located at a bag outlet connector, on the processing device.

The processing device may comprise a container of a washing liquid for injecting into the collecting bag. This washing liquid may be injected at a temperature close to body temperature. It may be warm or lukewarm water with, for example, at least one additive if desired. The washing liquid may be injected for example from a single point.

The processing device may comprise a system for injecting a lubricant such as vaseline as soon as odor is detected and/or during or at the end of evacuation or washing. Washing may be followed by drying by ventilation prior to the injection of lubricant.

The invention also relates, in another of its aspects, to an excreta processing assembly comprising:
 at least one collecting bag as defined above, and
 a processing device as defined above.

The assembly may comprise, if desired, a plurality of processing devices.

The processing devices may be located in different rooms and patients can be connected to any of the processing devices, depending on where they currently are.

One processing device may advantageously have several connection systems allowing several patients to be connected up to it simultaneously, as for example when these users are present in the same room.

As a variant, a processing device may comprise a single connection system, being designed for example to be located near a bed or armchair belonging to one patient. Such a processing device may be mobile, with limited autonomy, being for example reduced to a limited number of processing cycles. Such a device may be fitted to a bed, stretcher, armchair or walking frame, or to a vehicle allowing a person with reduced mobility to get about.

The processing device may, if required, run the processing cycle on the basis of personalized information such as for example the nature and volume of excreta.

The processing device may be designed to store information about its operation, such as the time and date a processing cycle was commenced, the type of excreta evacuated, nature of the odors detected, and the patient's name, it being possible for this information to be edited directly at the device or remotely.

The care staff can thus spot potential digestive or urinary problems of the patient.

The invention also relates, independently of the above or in combination with it, to a method for processing a patient's excreta by means of an assembly as defined above, in which the undergarment comprises inflatable cells, comprising the following steps:
 at least partly inflating all or some of the inflatable cells, and
 evacuating the excreta present in the collecting bag.

The inflatable cells on the user's side are preferably inflated before the cells underneath the user, in order not to destabilize the latter.

The cells may be inflated as soon as, for example, an odor representing the presence of excreta in the collecting bag is detected or, in a variant, the persistence of such an odor.

If appropriate, the processing device may be designed to be operated by the user, so that the latter can for example commence a processing cycle or just certain operations of this cycle, such as the prior inflation of the cells. Control may for example be through a remote control. Such a possibility can be useful for patients who do not suffer from incontinence but who have to stay in bed in order to reduce the burden on the care staff.

A washing liquid may be injected into the collecting bag before the excreta is evacuated.

The collecting bag may be forcibly ventilated following evacuation and washing in order to dry the user.

A lubricant may be injected into the collecting bag, especially after evacuation or during and after evacuation.

The process may end with the inflatable cells being deflated.

The invention also relates to the collecting bag considered in isolation, independently of the supporting part.

Figure 2:
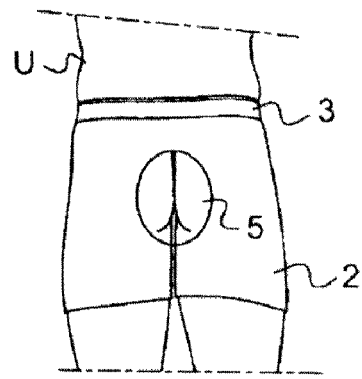
Figure 3:
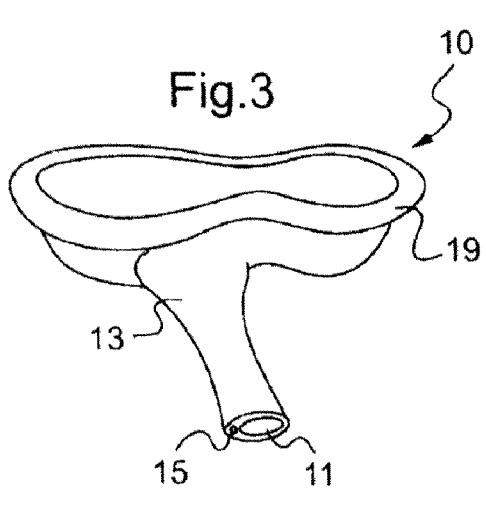
Figure 4:
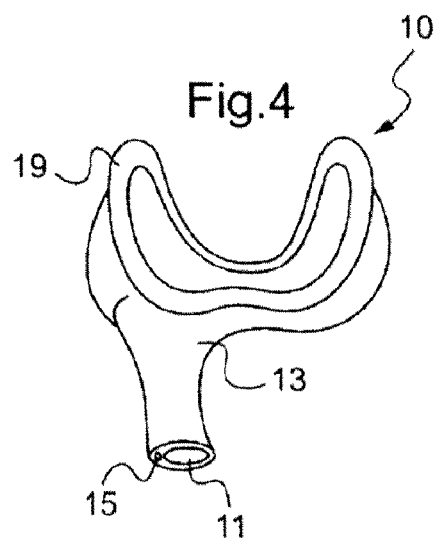
Figure 5:
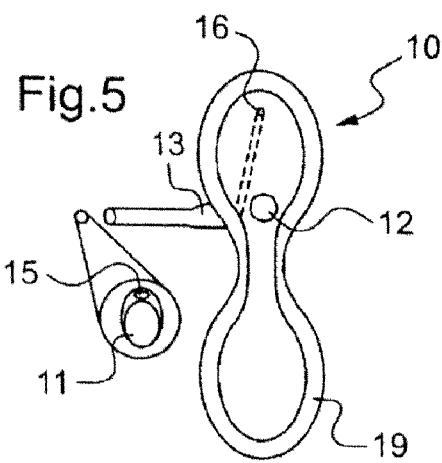
Figure 6:
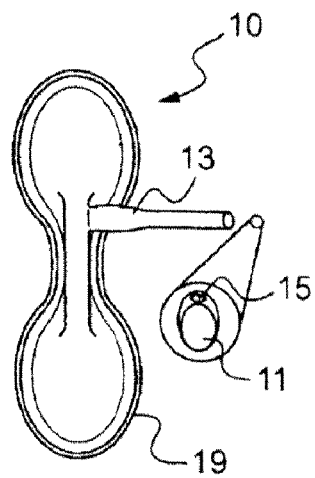
Figure 7:
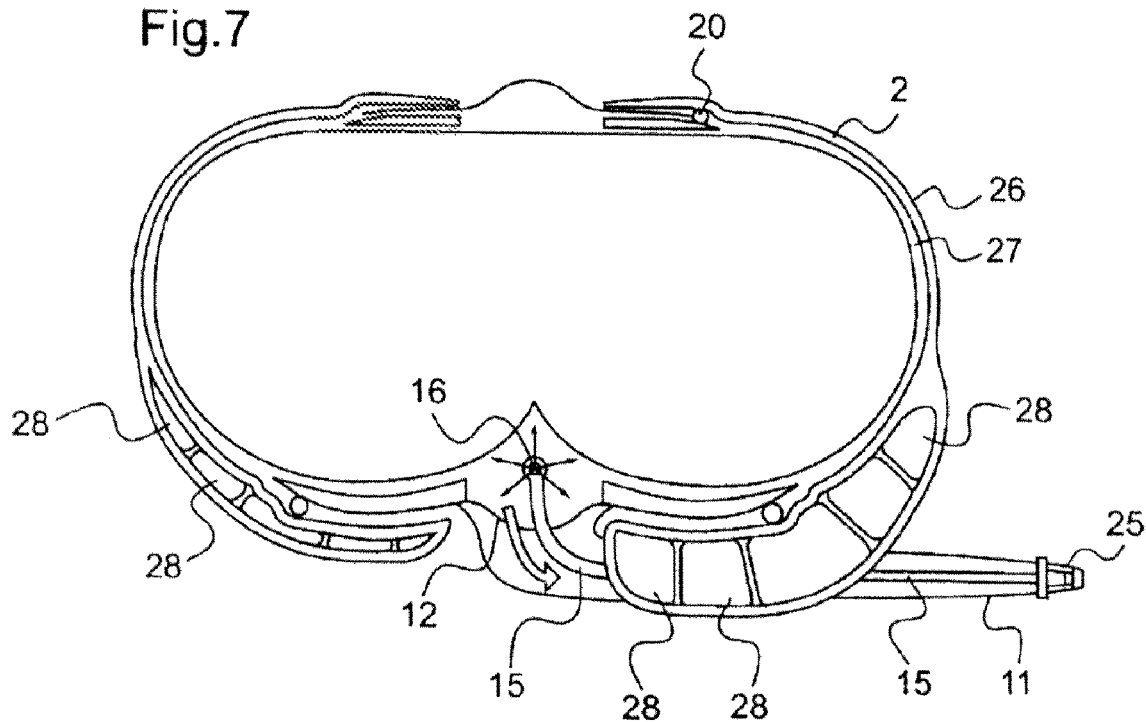
Figure 8:
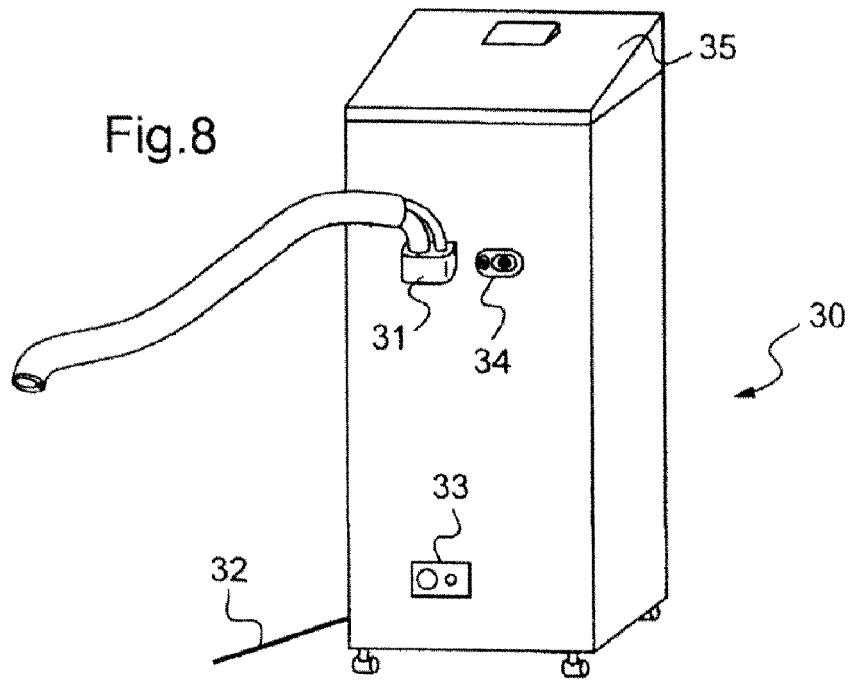
Figure 9:
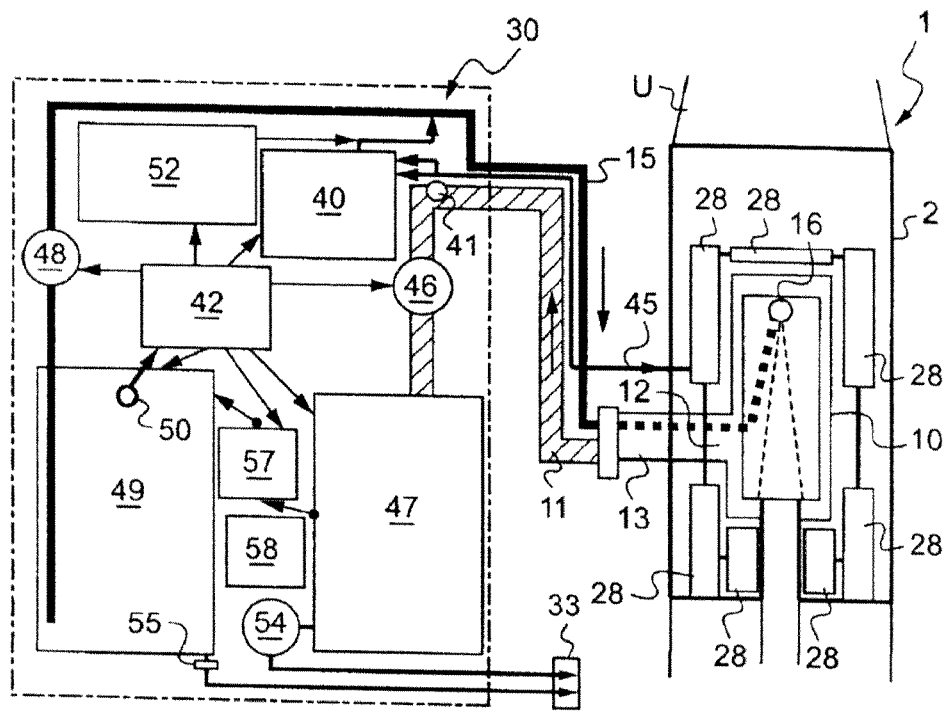
Figure 10:
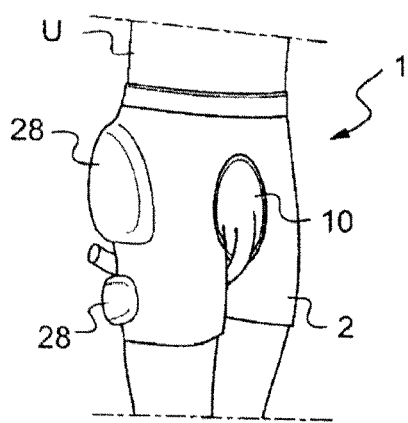
Figure 11:
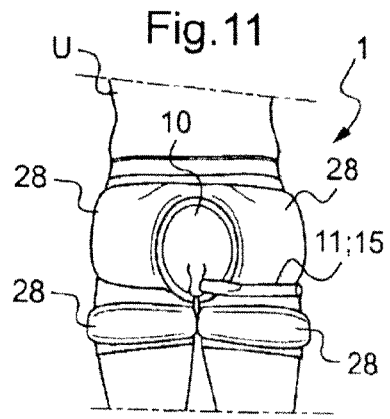
Figure 12:
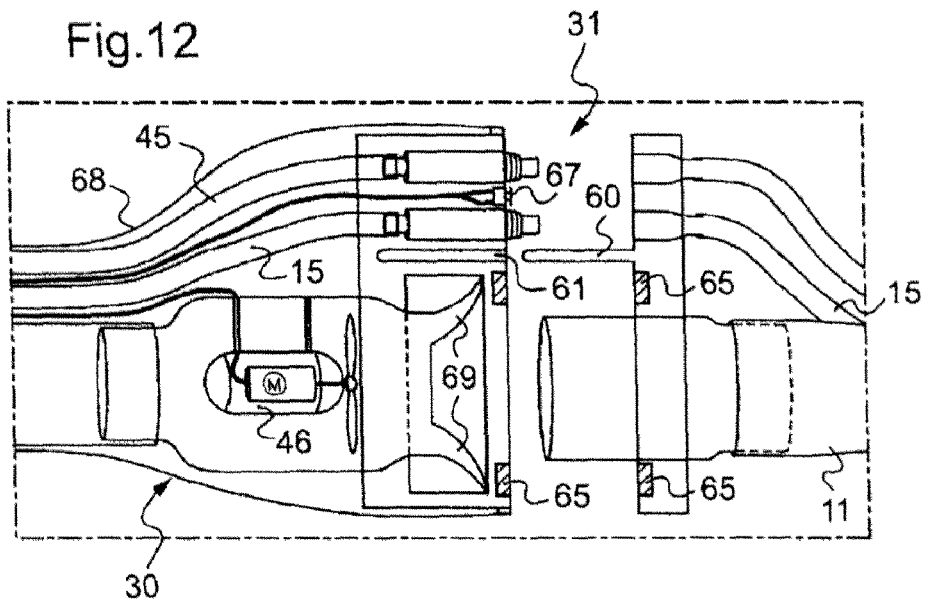
Figure 13:
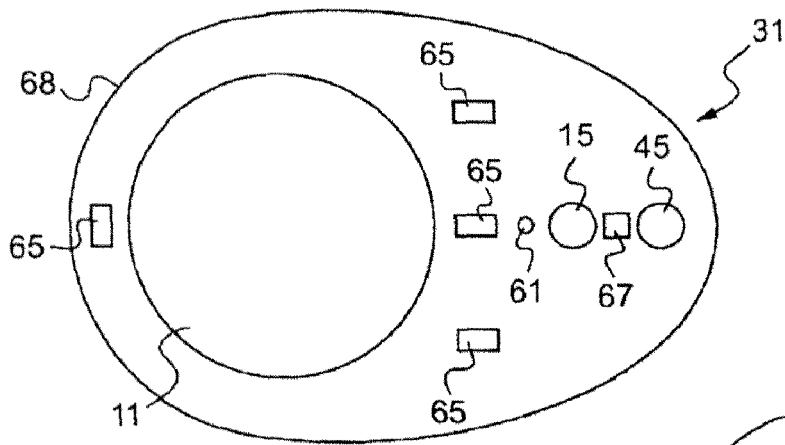
Figure 14:
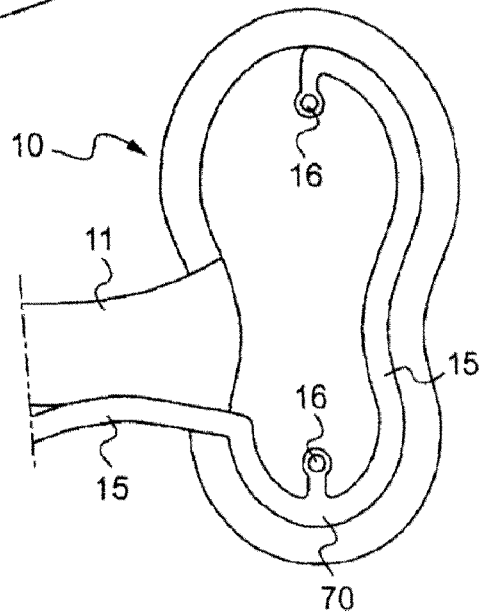

A clearer understanding of the invention may be gained from reading the following detailed description of an example of a non-limiting embodiment thereof, and by examining the attached drawings, in which:

FIG. 1 shows an undergarment in accordance with the invention,

FIG. 2 is a view similar to FIG. 1 of part of the undergarment seen in FIG. 1, FIGS. 3 and 4 are perspective views, the former in isolation and the latter in position on the user, of the collecting bag of the undergarment seen in FIG. 1, FIG. 5 is a top view of the collecting bag, FIG. 6 is a developed bottom view of the collecting bag, FIG. 7 is a schematic partial transverse section through a user wearing the undergarment, FIG. 8 is a partial schematic view of a processing device in accordance with the invention, FIG. 9 is a block diagram showing schematically and partially the operation of both the device and the undergarment, FIGS. 10 and 11 are perspective views, similar to FIG. 1, showing how the undergarment is worn, FIG. 12 is a partial schematic section through the connection of the undergarment in accordance with the invention to the processing device seen in FIG. 8, FIG. 13 is a front view of the processing device, showing the connection of the undergarment, and FIG. 14 shows a variant embodiment of the collecting bag.

FIG. 1 is a perspective view of a user U wearing an undergarment 1 according to the invention. It comprises a supporting part 2 similar to a pair of boxer shorts, made of a stretch material surrounding the hips and the top of each thigh.

The supporting part 2 preferably provides relatively gentle support pressure and can be held up by an elastic band 3 at the waist.

The supporting part 2 can be made of a woven or nonwoven material, preferably a textile material, washable and permeable to air and water vapor.

The supporting part 2 has an opening 5 in the crotch exposing the pubic and anal regions.

The undergarment 1 also has a flexible, collecting bag 10, shown in FIGS. 3-6, which is positioned in the opening 5 to cover this opening.

The collecting bag 10 is held in place in the opening 5 by, for example, inserting its perimeter 19 between the supporting part 2 and the skin of the user U.

A leaktight contact between the perimeter 19 and the skin can be insured simply by the pressure exerted by the supporting part 2. The undergarment may optionally comprise a seal 20 between the collecting bag 10 and the supporting part 2, as illustrated in FIG. 7. The seal may be inflatable, in which case it can be inflated for extra security in the event of detection of an odor.

The supporting part 2 comprises, in the example considered, two superposed layers 26 and 27 as illustrated in FIG. 7, separated by an air cushion comprising a plurality of interconnected inflatable cells 28. The outer layer 26 may provide moderate support and the inner layer 27 gentle support.

Once inflated, the cells 28 lift the patient's body off the bed or chair in such a way that the collecting bag and evacuation and injection tubes are no longer potentially compressed by the patient. The processing cycle will thus not be impeded.

At the same time, inflating the cells 28 and where appropriate the seal 20 enhances the sealing of the collecting bag 10 by pressing around its perimeter 19.

To aid an understanding of the invention, there is shown in FIG. 7 the left-hand half of the undergarment 1 with its cells 28 deflated and, on the right-hand side of FIG. 7, the inflated cells 28.

The collecting bag 10 is connected to the evacuation tube 11, which connects through an evacuation orifice 12 to the bag 10.

In the example illustrated, the evacuation tube 11 is produced as a single piece with the collecting bag. It would not of course be a departure from the present invention for another arrangement to be adopted, for example if the tube were to be heat-welded or adhesively bonded to the collecting bag or attached to it in some other way.

The evacuation tube 11 comprises, in the example described, a roughly funnel-shaped connecting portion 13 connecting it to the collecting bag 10. This connecting portion facilitates the evacuation of excreta present in the collecting bag to the evacuation tube 11.

The undergarment 1 also comprises an injection tube 15 which connects through an injection orifice 16 into the collecting bag 10. This injection tube 15 can be used to inject a washing liquid and/or lubricant and/or air for ventilation.

In the example illustrated, the evacuation tube 11 and injection tube 15 are joined together at the outlet of the collecting bag 10. They have a sheath in common, as illustrated in FIGS. 3-6.

The injection orifice 16 is located, in the example illustrated, at the top and rear of the collecting bag 10, and the evacuation orifice 12 at the bottom and rear of the bag 10.

The evacuation tube 11 is preferably flexible and elastically deformable, like the collecting bag 10. This enables them to be compressed when, for example, the user is sitting or lying down and to resume their shape when the user stands up or during micturition or defecation.

The collecting bag 10 may be thermoformed, being a plastic injection molding and in particular flexible. It may for example be low-density polyethylene. The evacuation tube 11 and injection tube 10 may be made of the same material.

The evacuation tube 11 may comprise, at its unattached end remote from the end connected to the collecting bag 10, means of attachment to the supporting part 2, for example toward the waist. It may for example be a hook-and-loop attachment type system such as a Velcro® strip.

In this way the end 25 of the evacuation tube 11 can be raised and attached to the supporting part 2 in such a way that excreta cannot be evacuated. This will allow the user to move about. To evacuate the collecting bag 10, the user simply lowers the end 25 of the evacuation tube 11, for example over the toilet.

The evacuation tube 11 can be closed by a cap comprising a moisture detector and fitted for example with a visual and/or audible and/or remote alarm configured to be triggered when a moisture threshold is exceeded.

The alarm may comprise for example an autonomous battery power supply. Staff or the patient can therefore be alerted by the alarm to the need to evacuate the collecting bag 10.

In an example of how the invention may be implemented, the undergarment is designed to be used in conjunction with a processing device 30 to which the end 25 of the tube 11 can be connected, as illustrated in FIGS. 8 and 9.

The processing device 30 shown schematically in FIG. 8 comprises an outer housing comprising a system 31 for connecting it to an undergarment and more particularly to the end 25 of the evacuation tube 11, an electric power supply 32, a connector 33 for the admission and discharge of water to the drain, a connector 34 for automatically washing the machine, and a control panel 35.

The processing device 30 comprises an air processing and inflation unit 40 for blowing air through the collecting bag. The incoming air flow passes through the injection tube 15 and injection orifice 16 and the outgoing air flow through the evacuation tube 11 and evacuation orifice 12, as shown in FIG. 9.

The moving air is analyzed by an odor sensor 41, such as an industrial gas sensor, notably of type 813, which is particularly sensitive to methane, propane and butane, and/or type 822, which is particularly sensitive to ammonia, sulfur dioxide, alcohol and hydrocarbons. An 813 type sensor can be used to detect excreta and gases and an 822 type sensor used to detect urine. Clearly, other sensors may be used.

Analysis of the air blown through the collecting bag will allow the presence of excreta to be detected, thereby causing the matter accumulated in the collecting bag to be evacuated when necessary.

The processing device 30 preferably has a central processing unit 42 with a microprocessor or microcontroller configured to analyze the information supplied by the sensor 41 and monitor the processing cycle.

The central processing unit 42 can be configured to determine whether the existence of an odor 41 is simply due to perspiration or flatulence, for example, in which case the excreta processing cycle is not commenced, or to the actual presence of excreta in the collecting bag.

To this end, the central processing unit 42 need only evacuate the excreta when a predefined odor persists for a predefined period, such as more than 2 minutes. In the absence of excreta, unpleasant odors are quickly evacuated by the air stream. If unpleasant odors are detected, the air flow rate can be briefly increased for a predetermined period, such as 1 minute, to ventilate the collecting bag more effectively and remove the uncertainty as to the origin of these odors.

The passage of air through the collecting bag allows, as has been seen, odors to be conveyed away for analysis by the sensor, and also allows a degree of drying of the collecting bag to prevent perspiration. Furthermore, this air stream will also dry the user's skin following evacuation and washing.

Besides all this, the air blowing and inflating unit allows the inflatable cells 28 to be inflated when necessary, that is, prior to the evacuation of excreta from the collecting bag 10. To this end, the inflation unit 40 is connected by an air supply tube 45 to the cells 28.

When excreta is detected by the processing device 30, the cells 28 are inflated.

The device 30 is preferably configured in such a way that the cells 28 on the user's side are inflated first as shown in FIG. 10, before the cells 28 located underneath the user, as shown in FIG. 11, where the user is seen from behind. The user is therefore not destabilized during inflation, and therefore remains comfortable during the evacuation operation.

The processing device 30 comprises a grinding pump 46 for transferring the excreta from the collecting bag 10 to a receiving vessel 47. The pump may be installed in the processing device and/or at the end 25 of the tube 11 where it connects to the processing device.

To facilitate the evacuation of excreta, a pump 48 may inject through the injection tube 15 and injection orifice 16 a washing liquid, stored for example beforehand in a tank 49.

For greater comfort, the washing liquid 49 is preferably injected at a temperature close to body temperature. This temperature is monitored by a temperature connector 50.

The tank 49 can be filled through a solenoid valve 55 via the connector 33.

Evacuation can also be facilitated by injecting lubricant through a spray unit 52, the lubricant being sprayed through the injection orifice 16. The lubricant can be sprayed very finely and transported into the bag, for example by the accelerated injection of air through the injection tube 15. Injection of lubricant can both facilitate the evacuation of excreta by the fact that the lubricant can coat the matter and facilitate their transport and, at the same time, the lubricant can help to prevent maceration in the collecting bag by the formation of a lipid layer to protect the skin and the mucous membranes.

Lubricant can be injected, for example, for a period of around 30 seconds.

The processing cycle can end with the deflation of the cells 28 under the control of the unit 40.

Matter collected in the container 47 can be evacuated by a pump 54 to the outside, especially to the drains, for example through the toilet via the connector 33 or by any permanent standard adapter.

In a variant embodiment, the processing device 30 may comprise a system 57 which recycles the matter collected in the container 47.

A recycling system 57 of this kind can be configured to allow the separation of liquids in the container 47 by allowing them to settle out. Solid matter can be pumped and injected under pressure into the disposable filter cartridge 58 which separates the fluid and the solid matter. Urine can be pumped into the disposable cartridge 58 provided for this purpose and stored therein. The collected fluid can then be passed along an ultraviolet sterilization tube before being re-injected into the washing liquid tank 49. If this variant is adopted, the tank 49 will preferably comprise an oily product. In this type of operation it may be unnecessary to inject lubricant as the washing liquid naturally comprises the oily product.

FIGS. 12 and 13 show an example of a system 31 for connecting the undergarment to the processing device 30.

The connection system comprises in this example a plug guide 60 designed to be inserted into a matching housing 61 in the processing device 30, to facilitate the engagement of the end of the undergarment with the processing device 30.

Additionally, in order to ensure that the connection is maintained, the undergarment and the processing device each comprise magnets 65 positioned face to face and magnetized appropriately to ensure that the connection is secure.

In the example described, the connection system 31 comprises four pairs of magnets 65.

The processing device 30 may also comprise an electrical contact 67 to allow the status of the connection to be transmitted to the microprocessor 42, that is to say, whether the collecting bag is or is not connected to the processing device 30.

The various tubes, namely the evacuation tube 11, the injection tube 15 and the inflation tube 45 for the inflatable cells, can be inserted into a flexible jacket 68 made of a synthetic fabric, for example.

The evacuation tube 11 of the collecting bag 10 is designed to be connected to the grinding pump 46 by a lip adapter 69, as can be seen in FIG. 12.

The invention is not limited to the particular example of an embodiment described above.

The shape of the supporting part 2 could in particular differ from that illustrated in FIG. 1. The supporting part might for instance take the form of a short-sleeved undersuit with a secure closure to prevent the patient from undressing at an inappropriate moment.

The supporting part 2 might also comprise a flap with or without an inflatable seal in the crotch to make the positioning and/or retention of the collecting bag easier.

In a variant, the supporting part 2 may have no opening 5 and the collecting bag 10 may in this case be inserted inside the supporting part. If appropriate, the supporting part 2 may be more extensible in the crotch so that the bag is not overcompressed.

The supporting part may of course be available in several sizes to fit all potential users, as may the collecting bag.

In the illustrative embodiment shown in FIGS. 1-6, the undergarment 1 has a single injection orifice 16 into the collecting bag 10, but it would not be a departure from the present invention if a different arrangement were adopted, for example if the injection tube 15 were connected through multiple injection orifices 16.

To give an example, FIG. 14 shows an illustrative embodiment in which the injection tube 15 connects to two injection orifices 16, one in front of the collecting bag and the other at the rear.

For this purpose the injection tube 15 comprises a portion which is welded to the collecting bag, to the periphery of the latter, as illustrated in FIG. 14, and a branch 70 defining two branch pipes, each leading to one of the injection orifices 16.

In the example illustrated in FIG. 14, the evacuation tube 11 has a conical shape where it connects to the collecting bag 10 and has a lip welded to a corresponding lip on the collecting bag. This is to ensure leaktight evacuation of the matter.

In an alternative embodiment of the invention, the undergarment may have no sensor. The sensor or sensors may be located in the processing device. This would be a way of reducing the cost of the undergarment.

In a variant, the undergarment and/or the processing device have no liquid sensor.

Additionally, the processing device 30 has been described as being connected to a network of injection and evacuation pipes, such as the drains and a water supply pipe, but it would not be a departure from the present invention if a different arrangement were adopted, for example if the processing device 30 were autonomous and able to function for a given number of cycles without being supplied with liquid and without requiring evacuation of liquid or solid matter. The processing device may for example be designed to perform at least five processing cycles autonomously. The recycling system may in this case be especially useful.

The processing device may if desired be built into a bed, a wheelchair or a stretcher.

To increase the autonomy of the processing device, the device may also have a rechargeable battery so that it does not depend on being connected to mains electricity.

The expression "comprising a" should be understood as synonymous with "comprising at least one", unless the contrary is specified.

The invention claimed is:
1. A system for processing excreta, comprising:
an undergarment configured to be worn by a patient comprising:
a support configured to surround at least the patient's hips and tops of each thigh;
wherein the support comprises two superposed layers and a plurality of inflatable cells positioned between the two superposed layers;
a flexible collecting bag positioned on the undergarment to cover both a pubic region and an anal region of the patient when the undergarment is worn;
an evacuation tube in fluid connection with an evacuation orifice associated with the collecting bag; and
a closure cap configured to close an end of the evacuation tube when the evacuation tube is not connected to a processing device, wherein the processing device comprises:
an excreta presence sensor; and
a processor for connection to the flexible collecting bag, wherein the processing device is configured to evacuate excreta from the collecting bag based on information supplied by the excreta presence sensor;
wherein the system is mobile.
2. The system as claimed in claim 1, wherein the support comprises an opening near the patient's crotch and the collecting bag is aligned at least partly with the opening.
3. The system as claimed in claim 1, in which the collecting bag is designed to be in contact with skin associated with the patient.
4. The system as claimed in claim 1, in which the collecting bag is designed to cover the perineal region of the patient.
5. The system of claim 1, wherein the collecting bag comprises a single piece with the evacuation tube.
6. The system of claim 5, wherein the evacuation tube comprises a funnel-shaped connecting portion connecting the evacuation tube to the collecting bag.
7. The system of claim 5, wherein the end of the evacuation tube is configured to be connected to the processing device.
8. The system of claim 1, wherein the evacuation tube is flexible and comprises an attachment structure to attach the evacuation tube to the support.
9. The system of claim 1, wherein the collecting bag is made by injection molding of a plastic.
10. The system of claim 1, further comprising a seal inserted between the collecting bag and the support.
11. The system of claim 1, in which the collecting bag is separable from the support.
12. The system of claim 1, comprising a removable connection structure between the collecting bag and the support.
13. The system of claim 1, in which the support comprises a textile material.
14. The system of claim 13, wherein the textile material comprises a stretch material.
15. The system of claim 1, in which the processing device is configured to inflate all or some of the cells before the excreta is evacuated.
16. The system of claim 1, the processing device further comprising a container of washing liquid for injecting into the collecting bag.
17. The system of claim 1, in which the processing device comprises a system for recycling material collected in a receiving container associated with the processor.
18. A method for processing excreta of a patient using the system of claim 1, comprising the following steps:
at least partly inflating all or some of the inflatable cells of the undergarment, and
evacuating the excreta present in the collecting bag of the undergarment.
19. The method of claim 18, wherein inflatable cells located on the patient's side are inflated before inflatable cells located underneath the patient.
20. The method of claim 18, in which a washing liquid is injected into the collecting bag before the excreta is evacuated.
21. The method of claim 18, in which the collecting bag is forcibly ventilated following evacuation.
22. The method of claim 18, in which a lubricant is injected into the collecting bag.
23. A system for processing excreta, comprising:
an undergarment configured to be worn by a patient comprising:
a support configured to surround at least the patient's hips and tops of each thigh; and
a flexible collecting bag positioned on the undergarment to cover both a pubic region and an anal region of the patient when the undergarment is worn;
an evacuation tube in fluid connection with an evacuation orifice associated with the collecting bag;
a closure cap configured to close the end of the evacuation tube when the evacuation tube is not connected to a processing device, wherein the closure cap comprises a moisture detector, the moisture detector comprising a visual and/or audible alarm configured to be triggered when a moisture threshold is exceeded;
wherein the processing device comprises:
an excreta presence sensor; and
a processor for connection to the flexible collecting bag, wherein the processing device is configured to evacuate excreta from the collecting bag based on information supplied by the excreta presence sensor.
24. A system for processing excreta, comprising:
an undergarment configured to be worn by a patient comprising:
a support configured to surround at least the patient's hips and tops of each thigh;
a flexible collecting bag positioned on the undergarment to cover both a pubic region and an anal region of the patient when the undergarment is worn; and
an injection tube in fluid connection through an injection orifice with the collecting bag;
an evacuation tube in fluid connection with an evacuation orifice associated with the collecting bag;
wherein the evacuation tube and the injection tube are joined together;
and
a processing device, comprising:
an excreta presence sensor; and
a processor for connection to the flexible collecting bag, wherein the processing device is configured to evacuate excreta from the collecting bag based on information supplied by the excreta presence sensor.
25. A system for processing excreta, comprising:
an undergarment configured to be worn by a patient comprising:
a support configured to surround at least the patient's hips and tops of each thigh; and
a flexible collecting bag positioned on the undergarment to cover both a pubic region and an anal region of the patient when the undergarment is worn; and a processing device, comprising:
- an excreta presence sensor;
- a processor for connection to the flexible collecting bag, wherein the processing device is configured to evacuate excreta from the collecting bag based on information supplied by the excreta presence sensor; and
- an air processing unit configured to generate an air flow through the collecting bag;

wherein the excreta presence sensor comprises an odor sensor.

26. The system of claim 25, in which the odor sensor is configured to detect an odor that may be linked to excrement, and upon such detection, cause the air processing unit to generate an increased amount of air for a predefined period.

27. The system of claim 26, in which the processing device is configured to evacuate the excreta in the event that a predetermined odor persists for a predefined period.

28. The system of claim 25, wherein the air processing unit is configured to generate an airflow through the collecting bag on a continuous basis.

29. A system for processing excreta, comprising:
an undergarment configured to be worn by a patient comprising:
- a support configured to surround at least the patient's hips and tops of each thigh;
- a flexible collecting bag positioned on the undergarment to cover both a pubic region and an anal region of the patient when the undergarment is worn; and
- an injection tube in fluid connection through an injection orifice with the collecting bag;

and
a processing device, comprising:
- an excreta presence sensor;
- a processor for connection to the flexible collecting bag, wherein the processing device is configured to evacuate excreta from the collecting bag based on information supplied by the excreta presence sensor; and
a lubricant spray system.

* * * * *